US00PP27276P3

(12) United States Plant Patent
Grosser

(10) Patent No.: US PP27,276 P3
(45) Date of Patent: Oct. 18, 2016

(54) ***CITRUS* ROOTSTOCK NAMED 'UFR-6'**

(50) Latin Name: ***Citrus reticulata* + *Poncirus trifoliata***
Varietal Denomination: UFR-6

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,570

(22) Filed: Jan. 22, 2015

(65) Prior Publication Data

US 2015/0237780 P1 Aug. 20, 2015

Related U.S. Application Data

(60) Provisional application No. 61/942,575, filed on Feb. 20, 2014.

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

PUBLICATIONS

PLUTO: Plant Variety Database, Jan. 13, 2015, citation for 'UFR-6'. 1 page.*
U.S. Appl. No. 14/544,424, filed Jan. 5, 2015, Grosser.
U.S. Appl. No. 14/544,425, filed Jan. 5, 2015, Grosser.
U.S. Appl. No. 14/544,423, filed Jan. 5, 2015, Grosser.
U.S. Appl. No. 14/544,427, filed Jan. 5, 2015, Grosser.
U.S. Appl. No. 14/544,571, filed Jan. 22, 2015, Grosser.
U.S. Appl. No. 14/544,572, filed Jan. 22, 2015, Grosser.
U.S. Appl. No. 14/545,063, filed Mar. 20, 2015, Grosser.
U.S. Appl. No. 14/544,573, filed Jan. 22, 2015, Grosser.
Grosser et al., "Protoplast fusion and citrus improvement," *Plant Breeding Reviews* 8:339-374, 1990.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora*-Diaprepes Complex via Greenhouse Screening," *Proc. Fla. State Hod. Soc.* 120:103-109, 2007.
Grosser et al., "Protoplast fusion for production of tetraploids and triploids: Applications for scion and rootstock breeding in citrus," *Plant Cell Tissue Organ Culture* 104:343-357, 2011.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UFR-6' is a new and distinct allotetraploid *citrus* rootstock for tree size control and improved disease resistance. 'UFR-6' has shown a positive reaction to the Huanglongbing disease (HLB, or *citrus* greening disease) in multiple experimental field trials. Scion trees grafted on this rootstock show a reduced frequency of infection and reduced disease symptoms once infected as compared to commercial diploid rootstocks.

6 Drawing Sheets

Latin name of the genus and species of the plant claimed: *Citrus reticulata*+*Poncirus trifoliata.*
Variety denomination: 'UFR-6'.

BACKGROUND OF THE INVENTION

The present invention relates to a new and distinct variety of *citrus* rootstock named 'UFR-6'. The Plant Improvement Team in Lake Alfred, Fla. has pioneered the development and testing of allotetraploid *citrus* rootstocks. 'UFR-6' (identified as "Changsha+50-7" in field trials) is an allotetraploid somatic hybrid produced by protoplast fusion. 'Changsha' mandarin (*Citrus reticulata*) is the embryogenic suspension culture parent (the source of parental protoplasts) and trifoliate orange '50-7' (*Poncirus trifoliata*) is the leaf parent (the source of protoplasts).

BRIEF SUMMARY OF THE INVENTION

'UFR-6' was selected as a potential *citrus* rootstock on the basis of its reduced tree size, ability to produce sweet orange fruit with high solids, and positive reaction to Huanglongbing disease (HLB, or *citrus* greening disease) in multiple experimental field trials. Sweet orange scion trees grafted onto 'UFR-6' are precocious bearing, and trees generally do not exceed 10 feet in height when fully grown, making this rootstock a good candidate for use in Advanced *Citrus* Production Systems that feature high density plantings (Grosser et al., 2011). 'UFR-6' is seedy and highly polyembryonic, making it amenable to standard nursery propagation practices for uniform liner production. 'UFR-6' has also exhibited good cold hardiness. Long-term performance of trees on this rootstock selection is unknown. Trees on 'UFR-6' are susceptible to *citrus* blight, but its blight tolerance appears to be better than 'Swingle' citrumelo, the most popular commercial *citrus* rootstock in Florida. True-to-typeness of 'UFR-6' through asexual propagation was demonstrated by planting cuttings from the original tree and a tree grafted to a somatic hybrid rootstock ('Hamlin'+rough lemon) in Osceola county, Fla. Seeds from this tree and the original tree are predominantly of nucellar origin and produce true-to-type seedlings.

BRIEF DESCRIPTION OF THE DRAWINGS

'UFR-6' is illustrated by the accompanying photographs, which show the tree's form, foliage, and fruit. The colors shown are as true as can be reasonably obtained by conventional photographic procedures. The photographs are of a tree approximately 8 years old. All figures were taken in December of 2013.

DETAILED BOTANICAL DESCRIPTION

Figure 1:
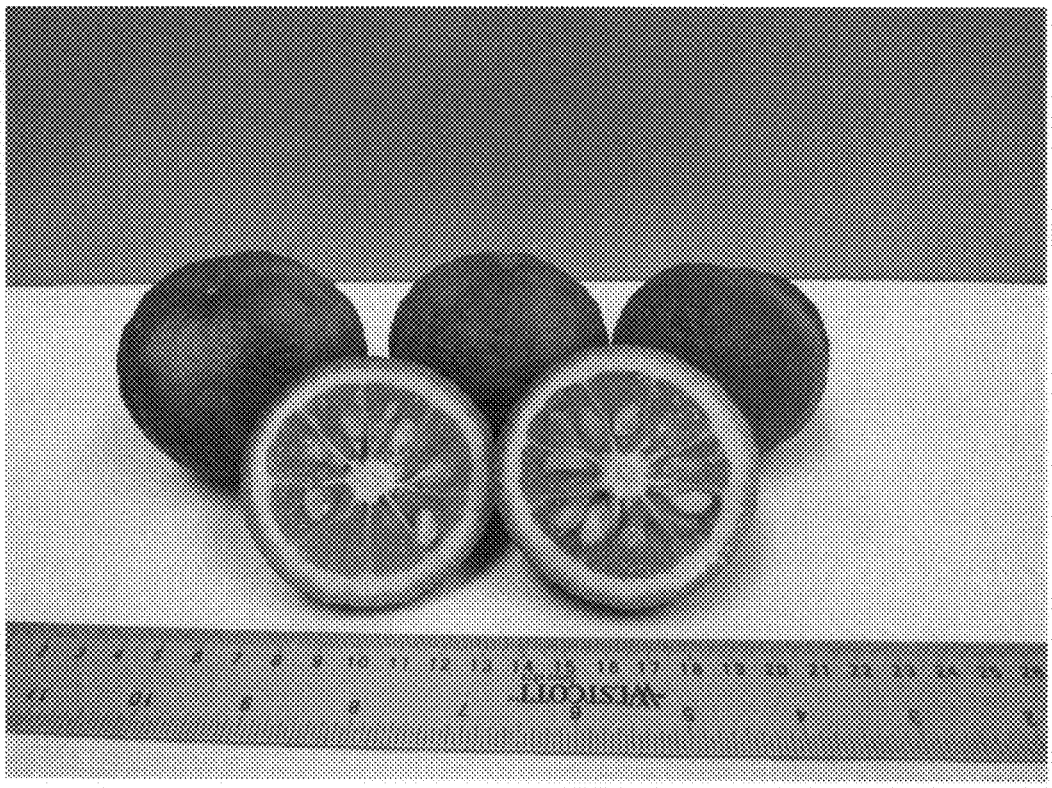
FIG. 1.—Shows a close-up of the nearly mature fruits with the rind and cross-sectional view of the fruit when cut in the center.
Figure 2:
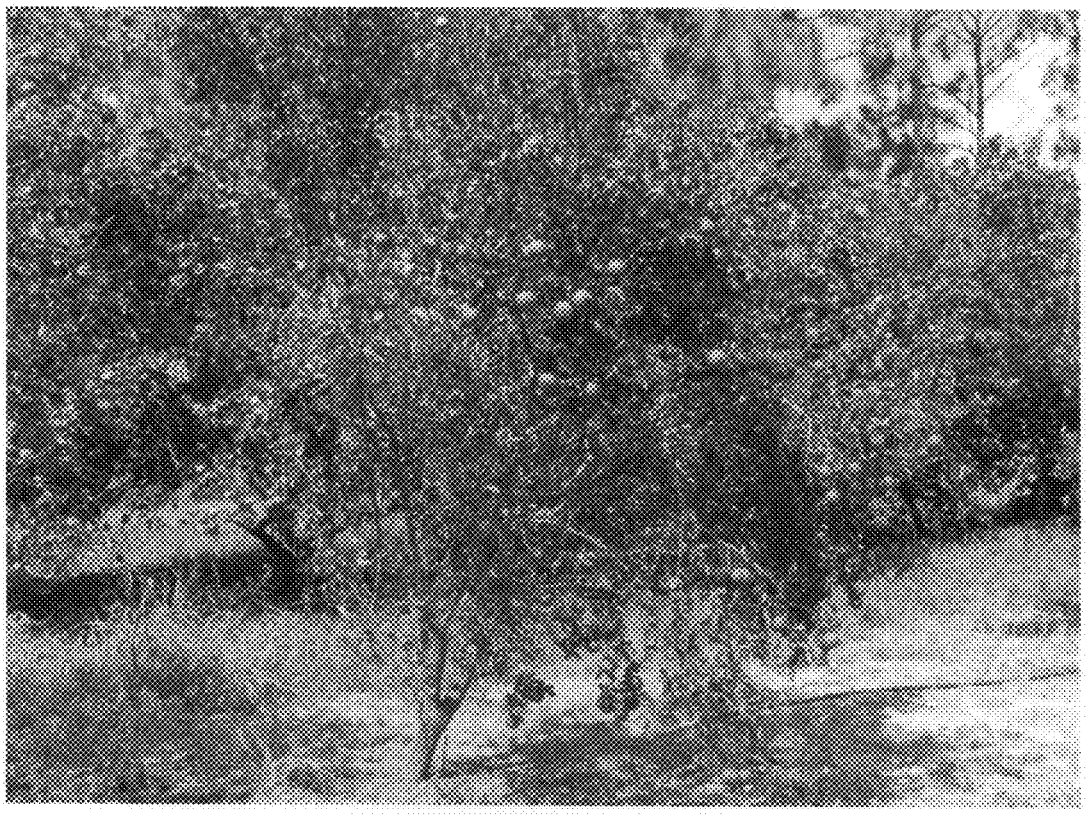
FIG. 2.—Shows the overall mature plant growth habit.
Figure 3:
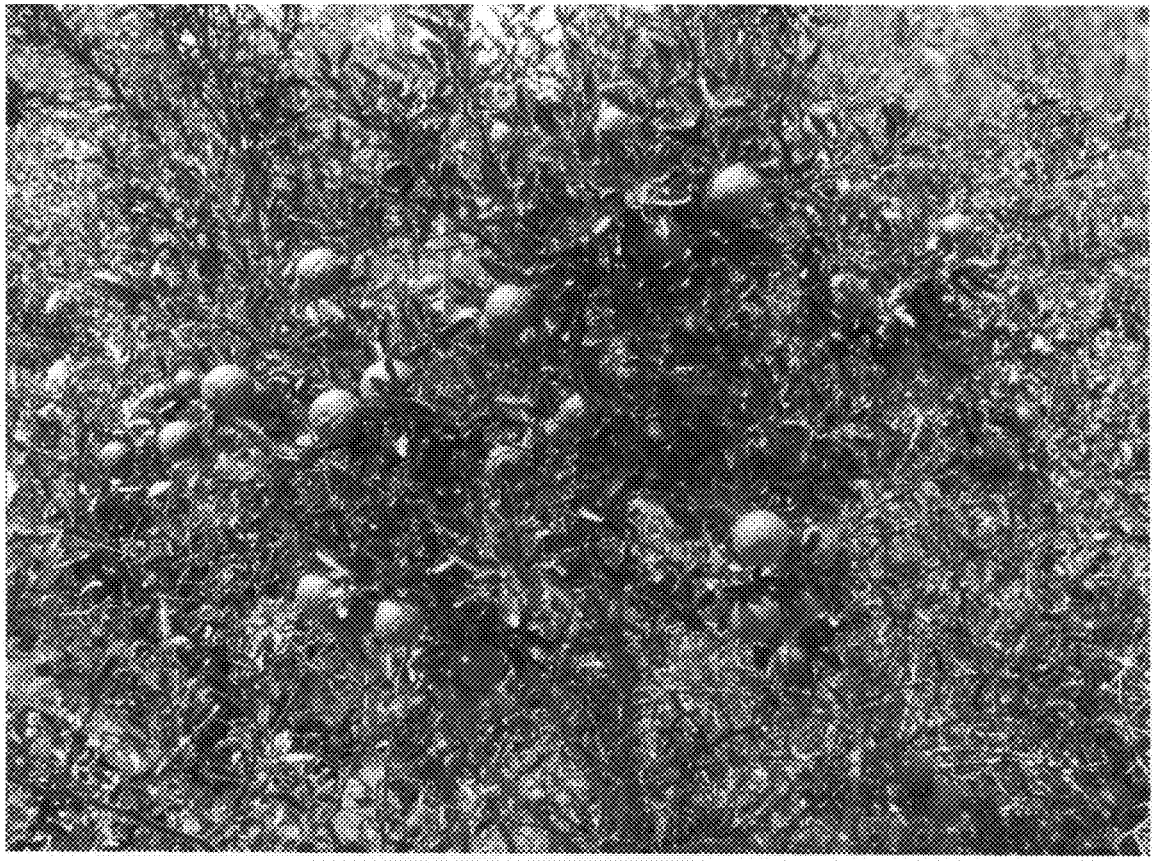
FIG. 3.—Shows nearly mature fruits hanging on the tree.
Figure 4:
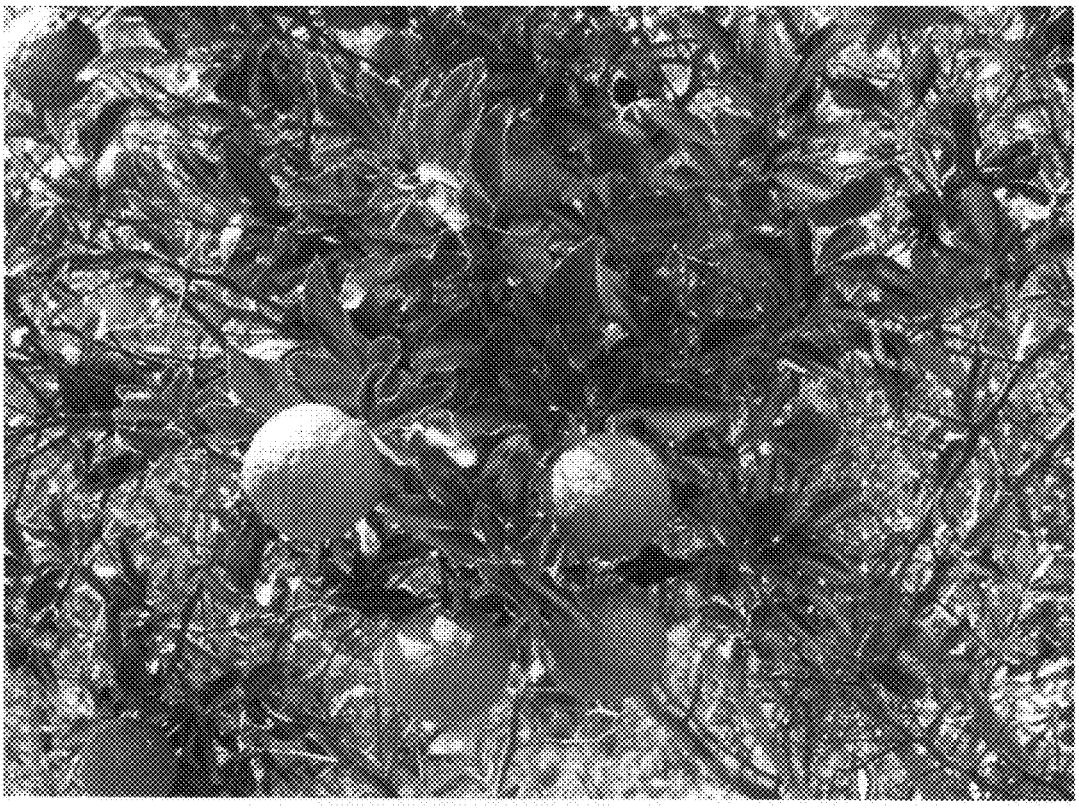
FIG. 4.—Shows leaves and nearly mature fruits.
Figure 5:
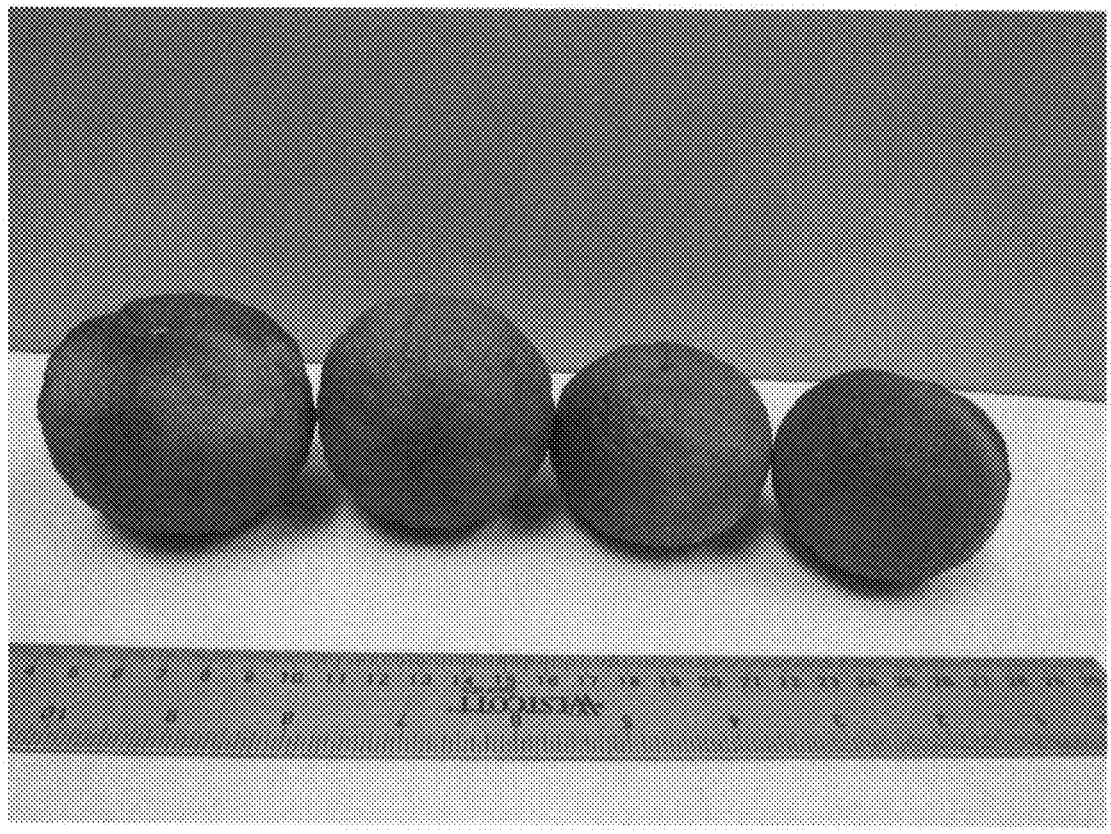
FIG. 5.—Shows a close-up of nearly mature fruits.
Figure 6:
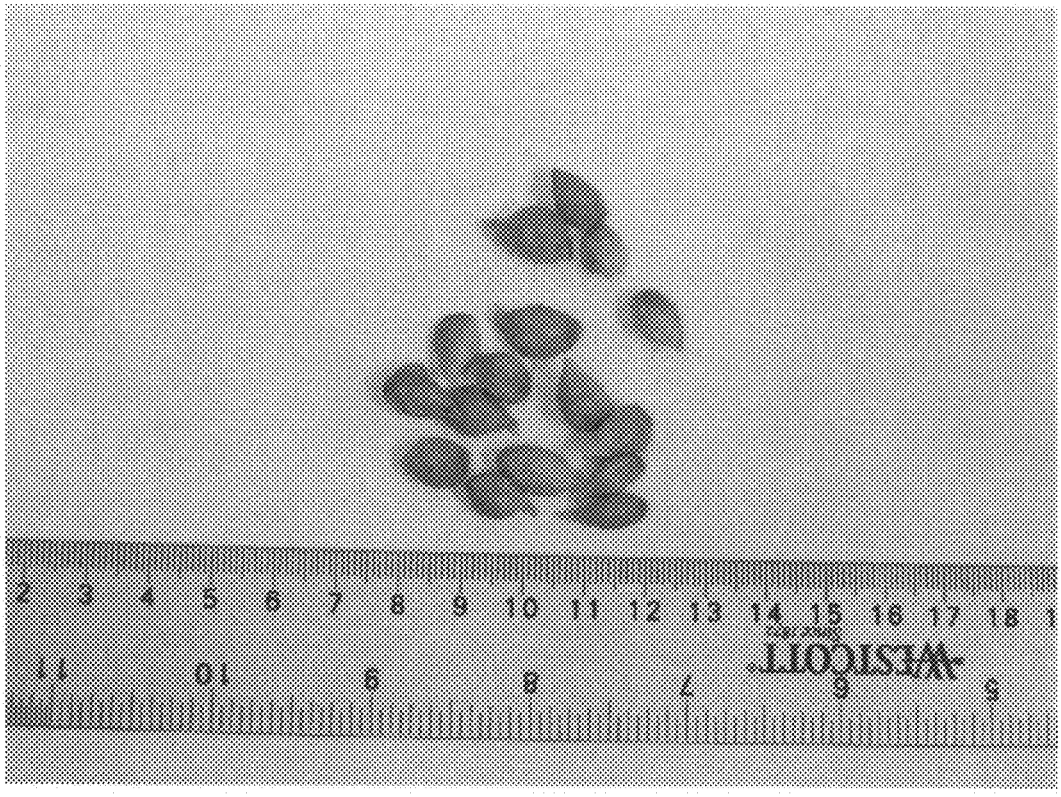
FIG. 6.—Shows a close-up of seeds from nearly mature fruit.

The following detailed description sets forth the distinctive characteristics of 'UFR-6'. The colors (except those in common terms) are described from The R.H.S. Colour Chart published by The Royal Horticultural Society in London (second edition), in association with the Flower Council of Holland.

PHENOTYPIC DESCRIPTION OF *CITRUS RETICULATA+PONCIRUS TRIFOLIATA* 'UFR-6'

Classification:

*Botanical.*—*Citrus reticulata+Trifoliate* orange *Poncirus trifoliate.*

*Common name.*—Allotetraploid somatic hybrid rootstock.

Parentage:

*Embryogenic culture parent.*—'Changsha mandarin' (unpatented).

*Leaf parent.*—'50-7 trifoliate orange' (unpatented).

Tree:

*Ploidy.*—Tetraploid.

*Size.*—Small.

*Height.*—3.3 meters.

*Tree spread.*—2.6 to 2.9 meters.

*Vigor.*—Moderately vigorous.

*Density.*—Canopies are moderately dense.

*Form.*—The tree is obloid-shaped with lateral and upright branches growing.

*Growth habit.*—Both upright and lateral growth with a low medium angle.

Trunk:

*Trunk diameter.*—10.9 cm in diameter at 30 cm above the ground on a 16-year-old tree.

*Trunk texture.*—Rough.

*Trunk bark color.*—RHS 197A (greyed-green); irregularly striated with RHS N189A (green).

Branches:

*Crotch angle.*—First crotch forms a 45- to 50-degree angle; middle crotch forms a 65-degree angle.

*Branch length.*—Branch reaches 2.8 meters from the first crotch to the tip of the branch.

*Branch texture.*—Relatively rough with small thorns or spines.

*Branch color* (*hoots from previous flush, hardened and* 4 *to* 5 *mm in diameter*).—RHS N137A (green).

Leaves:

*Size* (*lamina average*).—Length: 64.5 mm. Width: 39.1 mm. L/W ratio: 1.65.

*Thickness.*—Thicker than average diploid *citrus* rootstock hybrids.

*Type.*—Mostly simple leaf types, with trifoliate types of leaves appearing within the same tree.

*Shape.*—Elliptical.

*Apex.*—Retuse.

*Base.*—Acute to sub-obtuse.

*Margin.*—Entire and irregular margin, slightly undulate.

*Surface.*—Upper surface: Glabrous. Lower surface: Medium veins that are pinnately netted.

*Color.*—Upper surface (adaxial): RHS N137C (green). Lower surface (abaxial): RHS 138A (green).

*Petiole.*—Shape: Brevipetiolate (shorter than leaf lamina); junction between petiole and lamina is articulate. Width (petiole wing): Narrow. Shape (petiole wing): Obovate. Length: 16.1 to 18.1 mm. Width: 4.4 to 5.3 mm. Color: RHS N137C (green).

Flowers and flower buds:

*Type.*—Hermaphrodite.

*Bearing.*—Flowers grow from leaf axillaries and leaf terminals singly and in small clusters; most single flowers grow from leaf axillaries. Each flower branch consists of 4-8 flowers.

*Flower diameter.*—Fully open flower has an average diameter of 29.0 to 29.2 mm.

*Flower depth.*—Typical flower has an average depth of 22.1 mm.

*Flower blooming period.*—First bloom observed Mar. 18, 2014. Full bloom observed Mar. 25, 2014.

*Flower bud.*—Initial visible flower bud size: Length: 3.3 mm in length. Diameter: 3.4 mm in diameter. Mature flower bud size: Length: 16 mm in length. Diameter: 10.1 mm in diameter. Shape: Initial visible flower bud has a round ball shape; mature flower bud has an elongated olive shape. Color: RHS 145D (yellow-green) for initial visible flower bud; RHS NN155C (white) for mature flower bud, with few RHS 157D (green-white) spots distributed at tip of the flower bud.

*Flower petals.*—Shape: Flat, spatula-shaped. Apex shape: Smooth, acute-shaped. Base shape: Even obtuse. Color: Upper surface RHS NN155C (white); lower surface RHS NN155C (white), with RHS 157D (green-white) spots distributed toward to the petal apex. Margin: Smooth. Length: 22.7 to 23.5 mm. Width: 9.6 to 12.3 mm. Thickness: 0.5 to 0.6 mm. Texture: Medium soft, wrinkled.

*Flower sepal.*—Number: 5 per flower. Shape: Delta-shaped with an acute angle at the apex. Length: 4.9 mm. Width: 3.2 mm. Apex shape: Triangle-shaped. Margin: Smooth. Color: Upper surface RHS 145B (yellow-green); lower surface RHS 144B (yellow-green).

*Fragrance.*—Fragrant/Moderately fragrant.

*Flower pedicel.*—Length: 3.5 to 7.4 mm. Diameter: 1.4 to 2.1 mm. Color: RHS 145B (yellow-green).

*Reproductive organs.*—Fertility: Appears self-fertile. Pollen amount: Abundant/Moderate amount. Pollen color (general): Bright-yellow. Ovary shape: Oval-shaped.

Fruit:

*Size*.—Uniform.

*Height*.—56.5 to 61 mm on average.

*Width*.—63.8 to 71.2 mm on average.

*Average weight* (*per individual fruit*).—147 grams.

*Shape*.—Round.

*Shape* (*cross-section*).—Round.

*Apex*.—Truncated with slight dent.

*Apex cavity diameter*.—N/A.

*Base cavity diameter*.—5.0 to 6.5 mm.

*Base*.—No neck.

*Harvesting*.—Fruit can be harvested from October through December in Florida.

*Fruit stem* (*short stem connecting the fruit*).—Length: 5.8 mm. Diameter: 3.4 mm. Color: RHS 146A (yellow-green) with RHS 195B (grey-green) strip.

Rind:

*Adherence*.—Adherence between albedo (mesocarp) and flesh (endocarp) is strong. The adherence is evenly distributed from base to apex.

*Thickness*.—7.3 to 7.5 mm on average.

*Texture*.—Rough surface.

*Color*.—Flavedo (epicarp): Ranges between RHS N144A (yellow-green) to RHS 146A (yellow-green). Albedo (mesocarp): RHS N155B (white).

*Stylar end*.—Closed.

*Rind oil cell density*.—246 oil cells/square cm.

Flesh:

*Number of segments*.—Between 8 and 9 segments per fruit on average.

*Segment walls*.—Firm with sufficient strength to maintain integrity as separated.

*Juice*.—Abundant.

*Color*.—Uniformly RHS 16C (yellow-orange).

*Texture*.—Soft.

*Vesicles*.—Length: Arranged from 8.7 to 9.9 mm on average. Diameter (thickness): 3.0 to 3.8 mm on average.

*Eating quality*.—N/A.

*Juice index*.—Soluble solids (average): 8.5 Brix.

Seeds:

*Type*.—Polyembryonic/Monoembryonic.

*Number*.—Ranges from 30 to 37.

*Shape*.—Seed shapes are not uniform. Normal seeds are mostly ventricose/swollen-shaped and clavate club shaped.

*Size*.—Length: 15.9 to 16.4 mm. Width: 7.2 to 9.8 mm.

*Seed coat color*.—Outer Surface: RHS 156D (greyed-white) and wrinkled. Inner surface: RHS 165C (greyed-orange). Cotyledon color: RHS 145A (yellow-green).

Resistance to disease: 'UFR-6' rootstock was selected on the basis of its positive reaction to HLB disease (huanglongbing or *citrus* greening disease) in multiple field trials. Trees on this rootstock show a reduced frequency of infection and reduced disease symptoms once infected as compared to commercial diploid rootstocks.

What is claimed is:

1. A new and distinct *citrus* rootstock cultivar as illustrated and described herein.

* * * * *